United States Patent
Karunasiri et al.

(10) Patent No.: US 11,115,763 B2
(45) Date of Patent: Sep. 7, 2021

(54) LOW-POWER DIFFERENTIAL COMMUNICATION ARCHITECTURES

(71) Applicant: Advanced Bionics AG, Staefa (CH)

(72) Inventors: R. Tissa Karunasiri, Valencia, CA (US); Jie Yan, Valencia, CA (US); Scott Kenneth Arfin, Valencia, CA (US); Don Banh, West Hills, CA (US)

(73) Assignee: Advanced Bionics AG, Staefa (CH)

( * ) Notice: Subject to any disclaimer, the term of this patent is extended or adjusted under 35 U.S.C. 154(b) by 78 days.

(21) Appl. No.: 16/778,425

(22) Filed: Jan. 31, 2020

(65) Prior Publication Data

US 2021/0243537 A1 Aug. 5, 2021

(51) Int. Cl.
| | |
|---|---|
| *H04R 25/00* | (2006.01) |
| *H03L 7/081* | (2006.01) |
| *A61N 1/36* | (2006.01) |
| *A61N 1/372* | (2006.01) |
| *A61N 1/05* | (2006.01) |
| *H04B 1/40* | (2015.01) |

(52) U.S. Cl.
CPC ....... *H04R 25/554* (2013.01); *A61N 1/36038* (2017.08); *A61N 1/37276* (2013.01); *H03L 7/0812* (2013.01); *H04R 25/30* (2013.01); *A61N 1/0541* (2013.01); *H04B 1/40* (2013.01); *H04R 2225/021* (2013.01); *H04R 2225/67* (2013.01)

(58) Field of Classification Search
CPC ............ A61N 1/37276; A61N 1/36038; A61N 1/0541; H04R 25/554; H04R 25/30; H04R 2225/021; H04R 2225/67; H04B 1/40; H03L 7/0812
See application file for complete search history.

(56) References Cited

U.S. PATENT DOCUMENTS

| | | | | |
|---|---|---|---|---|
| 5,418,478 A | * | 5/1995 | Van Brunt | ......... H03K 17/6872 326/30 |
| 6,154,061 A | * | 11/2000 | Boezen | .................. H04L 25/028 326/86 |
| 7,777,641 B2 | | 8/2010 | Karunasiri | |
| 2020/0057462 A1 | * | 2/2020 | Karunasiri | .............. H04L 27/02 |

* cited by examiner

*Primary Examiner* — Brian Ensey
(74) *Attorney, Agent, or Firm* — ALG Intellectual Property, LLC (57) ABSTRACT

A device includes a voltage source configured to selectively drive a first wire and a second wire with a first voltage level. The device further includes an adjustable current source configured to selectively discharge the first and second wire. The device further includes a control circuit configured to output data and power by way of the first and second wire by selectively coupling the first wire to the voltage source and the second wire to the adjustable current source such that, during a first time period, the first wire has the first voltage level and the second wire has a second voltage level. The data and power is output by also selectively switching the couplings of the first time period such that, during a second time period subsequent to the first time period, the first wire has the second voltage level and the second wire has the first voltage level.

20 Claims, 5 Drawing Sheets

LOW-POWER DIFFERENTIAL COMMUNICATION ARCHITECTURES

BACKGROUND INFORMATION

Cochlear implants and other implantable medical devices are implanted in recipients to provide benefits for medical purposes. For example, cochlear implants may improve or enable hearing in a recipient lacking full hearing capabilities. Cochlear implant systems often include an external device that communicates with the cochlear implant. The external device may also include two components, which are configured to communicate with each other. The two components may be connected via a differential data link, but conventional differential data links may be relatively power hungry, produce unwanted radio frequency (RF) emissions, and/or have other disadvantages.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Low-power differential communication architectures are described herein. To illustrate, a system may include a device including a voltage source configured to selectively drive a first wire and a second wire with a first voltage level, the first and second wires included in a differential signaling wire pair. The device further includes an adjustable current source configured to selectively discharge the first wire and the second wire. The device further includes a control circuit configured to output data and power by way of the differential signaling wire pair by selectively coupling the first wire to the voltage source and the second wire to the adjustable current source such that, during a first time period, the first wire has the first voltage level and the second wire has a second voltage level less than the first voltage level and greater than zero volts. The data and power is output by also selectively switching the first wire from being coupled to the voltage source to being coupled to the adjustable current source and the second wire from being coupled to the adjustable current source to being coupled to the voltage source such that, during a second time period subsequent to the first time period, the first wire has the second voltage level and the second wire has the first voltage level.

The architectures, systems, and methods described herein may allow for communication between devices using low power and while also generating low levels of radio frequency (RF) emissions. For instance, a cochlear implant system using the architectures described herein may allow for a transmitter to be placed in a headpiece of the cochlear implant system rather than in a behind-the-ear (BTE) unit. Placing the transmitter in the headpiece allows for smaller BTE units, which may be advantageous for certain applications, such as for pediatric users. With the transmitter in the headpiece, data needs to be transmitted from the BTE to the headpiece. The low-power differential communication architectures described herein enable such communication while also providing power to the headpiece from the BTE using the same wire pair. This may allow for a reduction in thickness for a connector between the BTE and headpiece, as extra cables may be eliminated, providing a more flexible cable to the headpiece. These and other advantages and benefits of the present architectures, systems, and methods are described in more detail herein.

Various embodiments of low-power differential communication architectures will now be described with reference to the figures.

Figure 1:
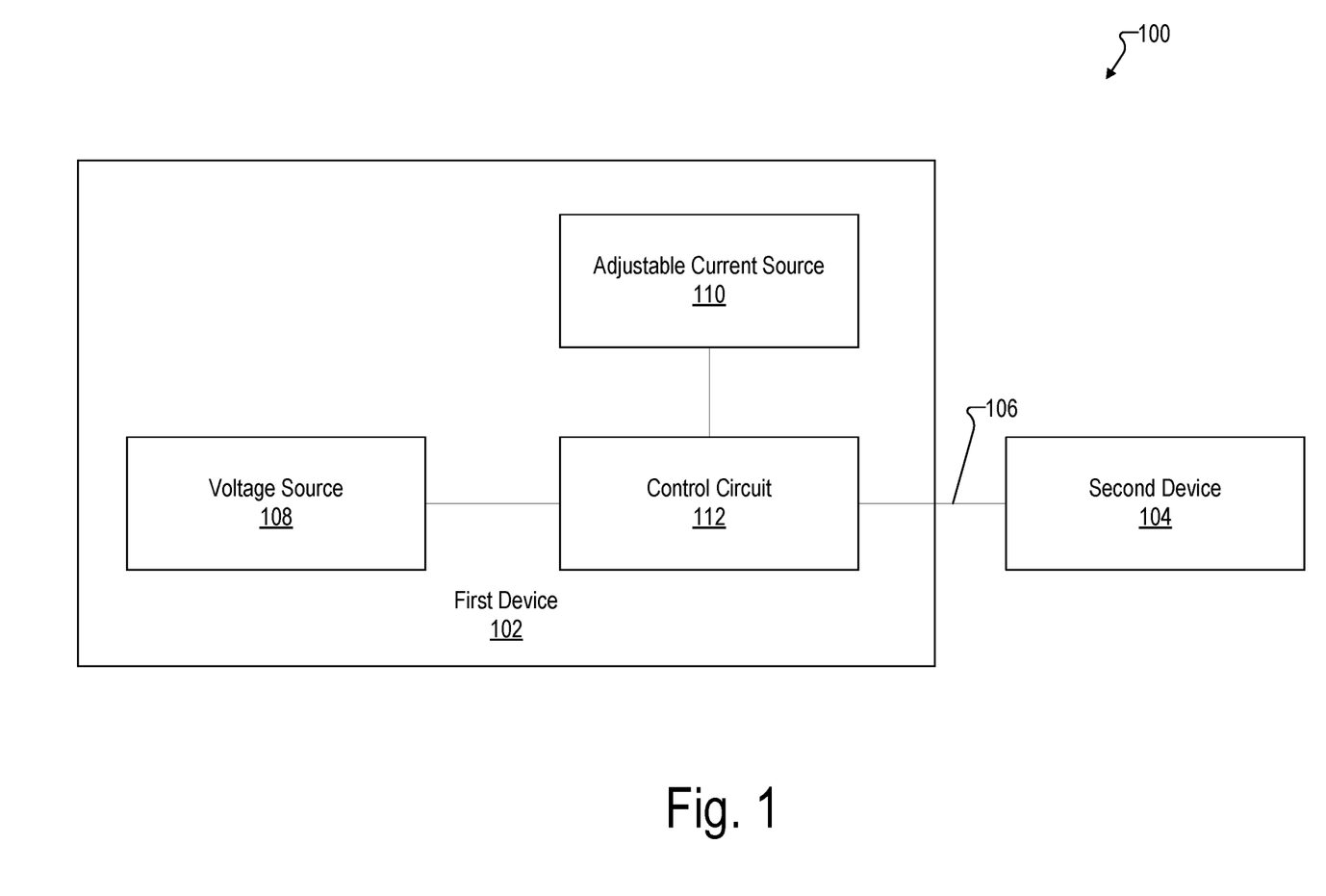
FIG. 1 illustrates an exemplary system according to principles described herein.

FIG. 1 illustrates an exemplary system 100 with a low-power differential communication architecture. System 100 includes a first device 102 and a second device 104. First device 102 and second device 104 may include any suitable devices configured to transmit and receive information. Examples of such devices are described herein.

First device 102 and second device 104 are connected to each other via a connector 106. Connector 106 may be any suitable connection between first device 102 and second device 104 that includes a first wire and a second wire so that first device 102 and second device 104 may communicate using differential signaling. For example, connector 106 may include a twisted wire pair, a cable including a plurality of wires (e.g., a coaxial cable), etc. In some examples, connector 106 may further include additional wires and/or components, such as a ground wire, a wire for back telemetry, etc. System 100 may include additional or alternative components as may serve a particular implementation.

First device 102 includes a voltage source 108, an adjustable current source 110, and a control circuit 112. Voltage source 108 may be implemented by a low-dropout (LDO) regulator, or any suitable component and/or circuit that provides a voltage. Adjustable current source 110 may be implemented by a binary weighted current source, such as a digital-to-analog converter (DAC), or any suitable component and/or circuit that provides an adjustable current. Adjustable current source 110 may be configured to function as a current sink to discharge voltage from wires connected to adjustable current source 110. Voltage source 108 and adjustable current source 110 are coupled to control circuit 112 to provide data to second device 104 via connector 106 using low-power differential signaling. In some examples, first device 102 may further be configured to provide power to second device 104 via connector 106 in addition to the data provided to second device 104.

For example, control circuit 112 may be configured to connect voltage source 108 to a first wire of connector 106 to set a voltage of the first wire to a first voltage level (e.g., a voltage output by voltage source 108) during a first time period. Control circuit 112 may be configured to also connect adjustable current source 110 to a second wire of connector 106 to discharge a voltage on the second wire to set the voltage of the second wire to a second voltage level during the first time period. These voltage levels on the first and second wires may be used for the differential signaling to second device 104. For instance, the first voltage level (a high voltage) on the first wire and the second voltage level (a low voltage) on the second wire may be configured to represent a high data signal and conversely, the first voltage level on the second wire and the second voltage level on the first wire may be configured to represent a low data signal. As the data signal switches from high to low, control circuit 112 may be configured to switch the connections such that voltage source 108 is connected to the second wire to set the voltage of the second wire to the first voltage level and adjustable current source 110 is connected to the first wire to set the voltage of the first wire to the second voltage level. Examples of control circuit 112 are described herein.

Figure 2:
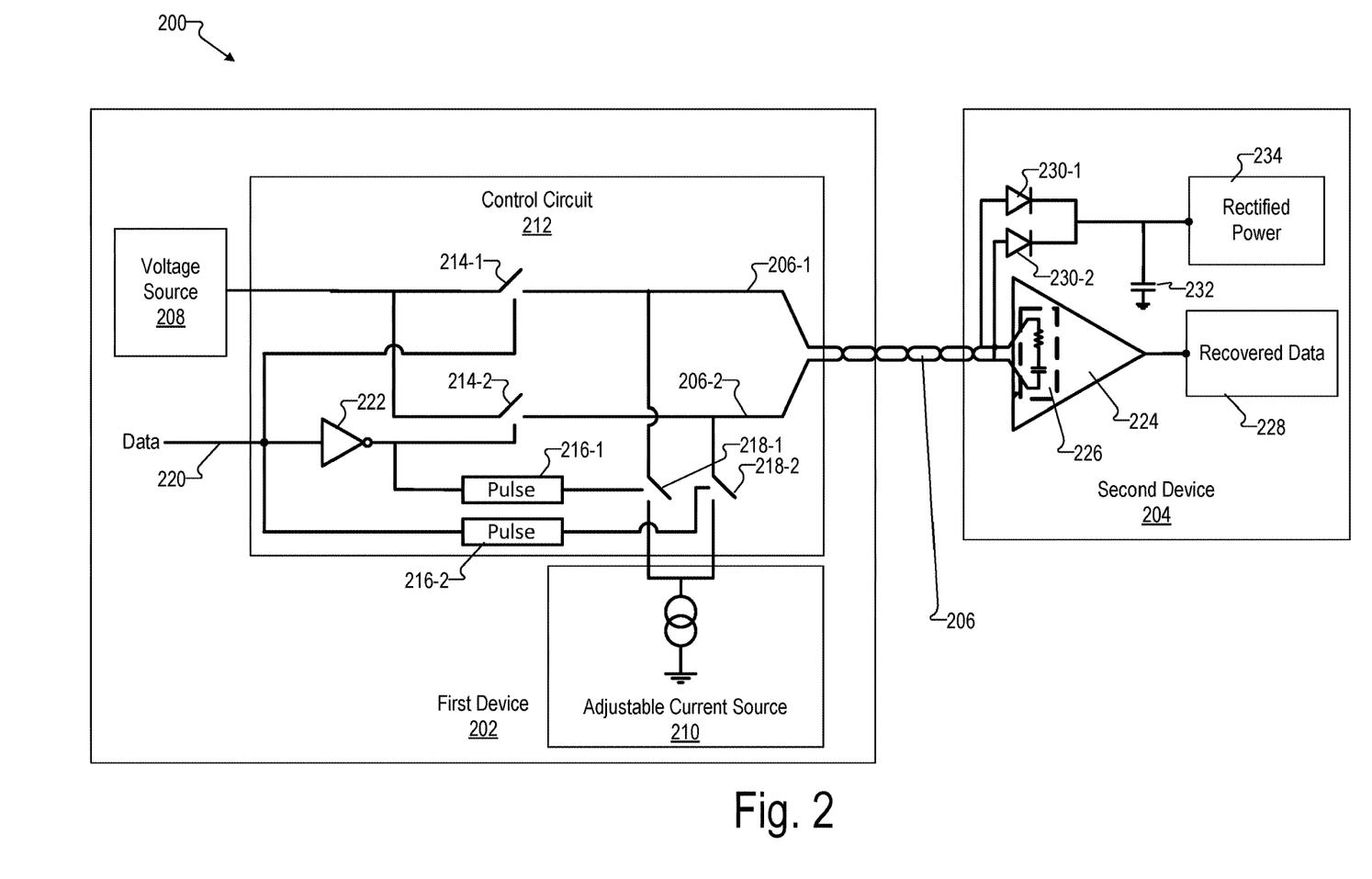
FIG. 2 illustrates an exemplary implementation of the system of FIG. 1 according to principles described herein.

FIG. 2 shows an exemplary implementation 200 of a system (e.g., system 100) with a low-power differential communication architecture. Implementation 200 includes a first device 202 (e.g., an implementation of first device 102) and a second device 204 (e.g., an implementation of second device 104) communicatively coupled by a connector that includes wires 206 (e.g., an implementation of connector 106 that includes a first wire 206-1 and a second wire 206-2). First device 202 includes a voltage source 208 (e.g., an implementation of voltage source 108), an adjustable current source 210 (e.g., an implementation of adjustable current source 110), and a control circuit 212 (e.g., an implementation of control circuit 112).

As shown, wires 206 include first wire 206-1 and second wire 206-2, which control circuit 212 is configured to set to a first voltage level and a second voltage level, respectively, to provide data using differential signaling. For example, during a first time period, control circuit 212 may be configured to set first wire 206-1 to the first voltage level by closing a switch 214-1 to connect first wire 206-1 to voltage source 208. Voltage source 208 may be configured to output the first voltage level. Depending on a state (e.g., a position) of switches 214 (e.g., switch 214-1 and switch 214-2), voltage source 208 may be configured to selectively drive first wire 206-1 and second wire 206-2 with the first voltage level. During the first time period, control circuit 212 may be further configured to close a switch 218-2 to connect second wire 206-2 to adjustable current source 210. Depending on a state of switches 218 (e.g., switch 218-1 and switch 218-2), adjustable current source 210 may be configured as a current sink to selectively discharge first wire 206-1 and second wire 206-2 to the second voltage level. Thus, during the first time period, first wire 206-1 may be set to the first voltage level and second wire 206-2 set to the second voltage level.

With first wire 206-1 set to the first voltage level and second wire 206-2 set to the second voltage level during the first time period, first device 202 may communicate to second device 204 a high data signal. At a second time period subsequent to the first time period (e.g., when first device 202 is to communicate to second device 204 a low data signal), control circuit 212 may be configured to switch the voltage levels on wires 206. For example, control circuit 212 may open switch 214-1 and switch 218-2 and close switch 214-2 and switch 218-1. By closing switch 214-2 and opening switch 218-2, voltage source 208 is connected to second wire 206-2 to set second wire 206-2 to the first voltage level. Meanwhile, adjustable current source 210 is connected to first wire 206-1 and sets first wire 206-1 to the second voltage level.

Control circuit 212 may set wires 206 to the second voltage level using adjustable current source 110 in any suitable manner. As shown, control circuit 212 includes pulse circuits 216 (e.g., pulse circuit 216-1 and 216-2) that are configured to control switches 218 (e.g., switch 218-1 and 218-2, respectively). By connecting one of wires 206 that is set to the first voltage to adjustable current source 210 for a known period of time and outputting a known current, control circuit 212 may discharge the wire from the first voltage level to set the wire to any suitable second voltage level. Examples of pulse circuits 216 are described herein. Additionally or alternatively, control circuit 212 may be configured to measure a voltage level on the wire (e.g., using a comparator) and open switches 218 when the voltage level on the wire is set to the second voltage level. Additionally or alternatively, control circuit 212 may control adjustable current source 210, such as by adjusting a current output by adjustable current source 210 and/or switching on and off adjustable current source 210 to set the wire to the second voltage level. In some examples, once the voltage level on the wire is set to the second voltage level, switches 218 are opened (and/or adjustable current source 210 is turned off), and a capacitance on the wire holds the voltage level on the wire floating at (or near) the second voltage level for a period of time. The period of time may be longer than a length of a data signal interval and/or a suitable number of data signal intervals (e.g., five data signal intervals for an 8b/10b encoding scheme) so that floating the wire at the second voltage level may effectively provide a differential signal to communicate a data signal to second device 204.

Control circuit 212 may be configured to receive a data signal at an input 220 that first device 202 is communicating to second device 204. The data signal may be configured to control switches 214 and pulse circuits 216 as shown to control the voltage levels on wires 206 to correspond to a state (e.g., high or low) of the data signal. For example, as shown the data signal directly controls switch 214-1 and pulse circuit 216-2, so that when the data signal is high, switch 214-1 is closed and switch 218-2 is closed for a pulse duration as controlled by pulse circuit 216-2. Further, the data signal is fed through an inverter 222, so that with the high data signal switch 214-2 is opened and pulse circuit 216-1 is inactive, leaving open switch 218-1. In this manner, first wire 206-1 will be set to the first voltage and second wire 206-2 will be set to the second voltage. When the data signal flips to a low signal, the states of switches 214 and 218 will be flipped, setting first wire 206-1 to the second voltage and second wire 206-2 to the first voltage.

At second device 204, the voltage levels on wires 206 may be received and interpreted to determine the data signal. For instance, second device 204 includes a comparator 224, which includes a capacitive termination circuit 226. Comparator 224 may receive the voltage levels on each of wires 206-1 and 206-2 to interpret the differential signal communication sent by first device 202. Thus, when comparator 224 receives the first voltage on first wire 206-1 and the second voltage on second wire 206-2, comparator 224 may interpret the voltages as a high data signal. Conversely, when comparator 224 receives the first voltage on second wire 206-2 and the second voltage on first wire 206-1, comparator 224 may interpret the voltages as a low data signal. Comparator 224 may output the interpreted signals as recovered data 228, which may correspond to the high and low data signals received by first device 202 at input 220.

In some examples, first device 202 is further configured to provide power to second device 204 via the first and second voltage levels on wires 206. The first voltage level provided by voltage source 208 and/or the second voltage level set by selectively connecting to adjustable current source 210 may be selected such that either or both may provide power to second device 204. For instance, as shown, second device 204 includes a pair of diodes 230 (e.g., diode 230-1 and 230-2) that may be configured to rectify power received via first wire 206-1 and second wire 206-2. Diodes 230 are coupled to a capacitor 232 and an output 234 at which the rectified power may be supplied. In other embodiments, diodes 230 are replaced by synchronous switches controlled by a clock and data recovery circuit to perform synchronous rectification.

While an example implementation of control circuit 212 is shown in system 200, control circuit 212 may include additional components, fewer components, and/or alternative components configured to selectively drive wires 206 with a first voltage source via voltage source 208 and selectively discharge wires 206 to a second voltage source via adjustable current source 210.

Figure 3A:
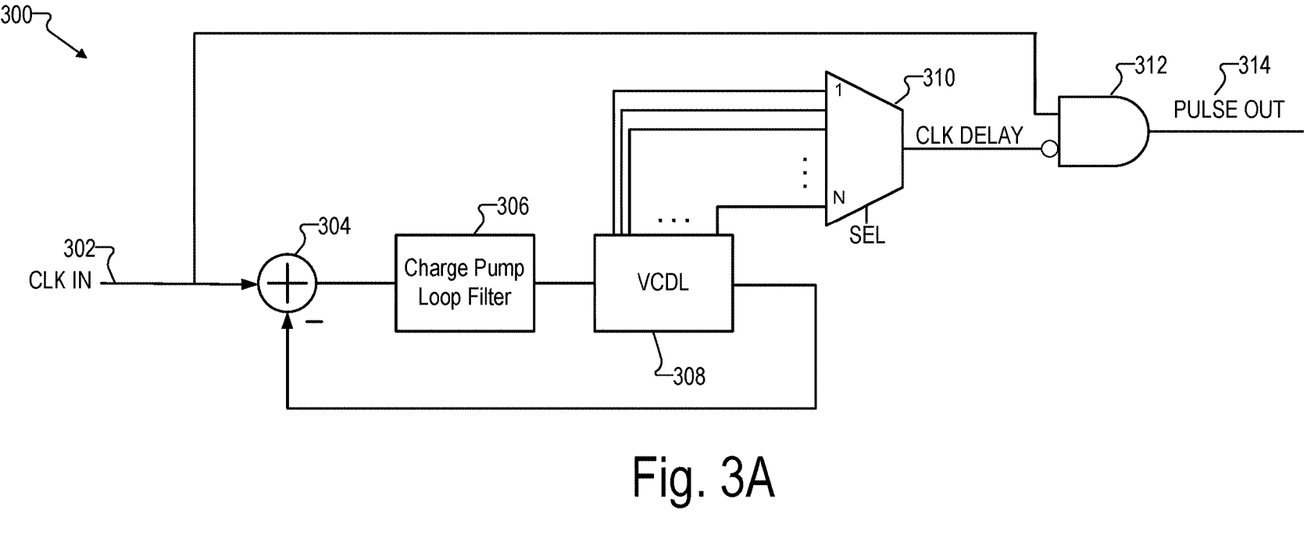
FIG. 3A illustrates an exemplary circuit of a device according to principles described herein.

FIG. 3A illustrates an exemplary pulse circuit 300, which may be an implementation of pulse circuits 216. Pulse circuit 300 includes an input 302 at which pulse circuit 300 receives a clock signal (CLK IN). Pulse circuit 300 further includes a phase detector 304, which is coupled to a charge pump and loop filter 306, which is coupled to a voltage-controlled delay line (VCDL) 308. VCDL 308 outputs back to phase detector 304 as well as to a selector 310. The output to selector 310 may be individual outputs for each of the delay line elements in VCDL 308. Selector 310 may be configurable to allow a user to calibrate a pulse width of pulse circuit 300. An output of selector 310 may be inverted and coupled with the CLK IN signal via an AND gate 312. An output of AND gate 312 may provide a pulse signal (PULSE OUT) at an output 314 of pulse circuit 300.

Figure 3B:
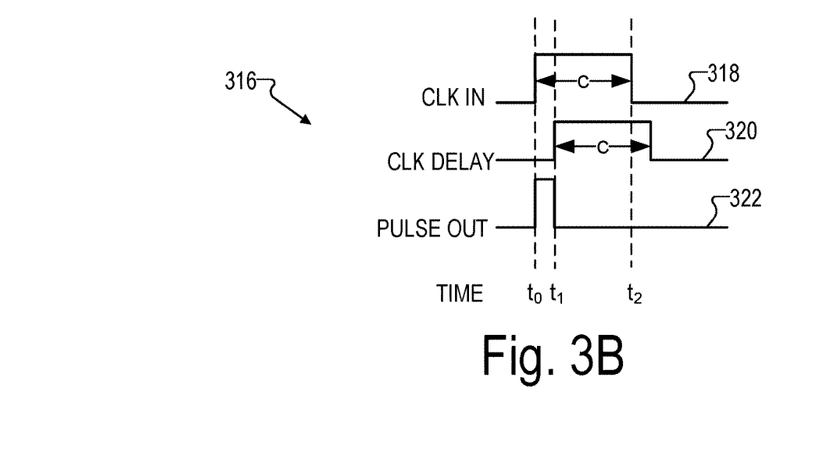
FIGS. 3B and 4 illustrate exemplary timing diagrams according to principles described herein.

FIG. 3B illustrates an exemplary timing diagram 316 of signals of pulse circuit 300. For instance, timing diagram 316 shows a line 318 for an input to pulse circuit 300 (CLK IN), a line 320 for an output of selector 310 (CLK DELAY), and a line 322 for an output of pulse circuit 300 (PULSE OUT). CLK IN may be provided by a data signal, such as the data signal received at input 220 in system 200. Line 318 shows CLK IN is received as a high signal at time $t_0$. As shown in timing diagram 316, CLK IN may have a length of time interval c, which may thus correspond to a data cycle interval. Line 320 shows the CLK DELAY signal, which is the CLK IN signal delayed by a time $t_1$. As mentioned, time $t_1$ may be configurable based on parameters of selector 310. CLK DELAY is a same length, time interval c, as CLK IN, delayed by the time $t_1$. As AND gate 312 receives the CLK IN signal with a negated CLK DELAY signal, PULSE OUT corresponds to line 322 as shown, outputting a high signal from time $t_0$ to $t_1$ and a low signal throughout a rest of the data cycle. As time $t_1$ is configured using selector 310, a pulse width ($t_1-t_0$) of PULSE OUT is configurable. Configuring the pulse width of pulse circuit 300 allows a control circuit (e.g. control circuit 212) to configure a length of time a wire is connected to an adjustable current source and thus configure a second voltage level to which the wire is discharged.

Figure 4:
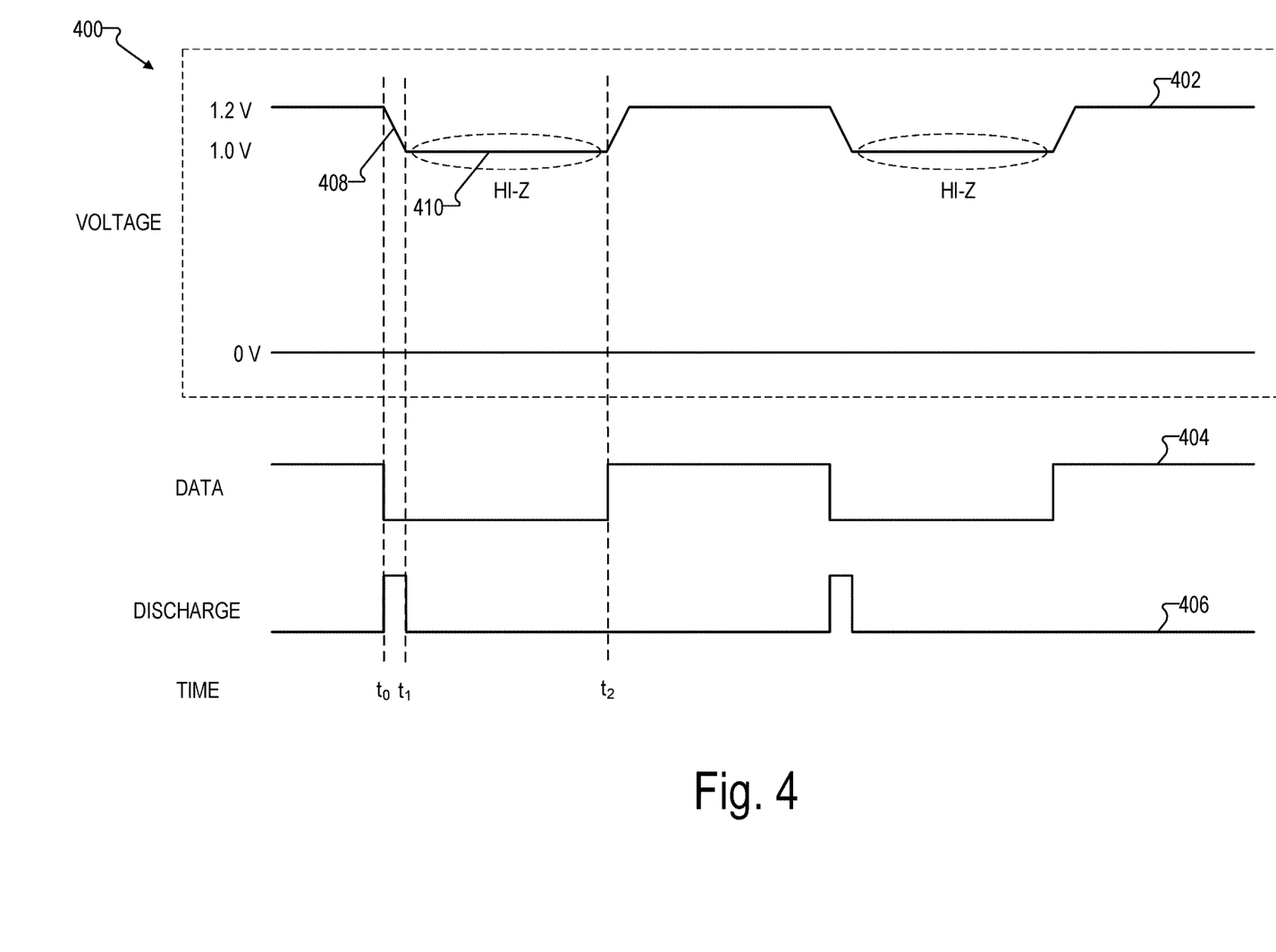

FIG. 4 illustrates an exemplary timing diagram 400. Timing diagram 400 shows an output on a wire (e.g., first wire 206-1) corresponding to a received data signal (e.g., the data signal received on input 220), as well as a discharge time (e.g., corresponding to an output of pulse circuit 216-1 (e.g., pulse circuit 300)). A line 402 shows a voltage level on first wire 206-1, which is set to a first voltage level (e.g., 1.2 volts (V)) and a second voltage level (e.g., 1.0 V) corresponding to the data signal, shown by a line 404. A line 406 shows the discharge time, which may correspond, for example, to PULSE OUT shown in timing diagram 316 as output by pulse circuit 300.

As shown, the voltage level on first wire 206-1 is set to the first voltage level (1.2 V) when the data signal is high and the second voltage level (1.0 V) when the data signal is low. Second wire 206-2 may be set to the opposite voltage levels for the corresponding data signal (not shown). The voltage level may be set to the second voltage level by discharging the voltage on first wire 206-1 for a time interval as shown by the discharge time (e.g., a time interval of a pulse width $t_1-t_0$). As mentioned, the pulse width may be configured for the pulse circuit, which may determine for how long the voltage on first wire 206-1 is discharged. Additionally, an output current level for an adjustable current source (e.g. adjustable current source 210) may also be configured, which may determine how quickly the voltage on first wire 206-1 is discharged. The second voltage level may be selected by controlling these (and any other suitable) characteristics of the adjustable current source. As shown, line 402 has a transitional edge 408 from the first voltage level to the second voltage level during the discharge time from $t_0$ to $t_1$. Varying the pulse width and the output current level may vary transitional edge 408. For example, a higher output current level may act as a greater current sink, resulting in a transitional edge that is steeper than transitional edge 408. Conversely, a lower output current level may result in a more shallow transitional edge than transitional edge 408. The pulse width may also be varied accordingly to discharge the voltage level to a desired second voltage level. In some examples, a steeper transitional edge may be advantageous for detection of voltage transitions at a second device (e.g., second device 204), while a more shallow transitional edge may be advantageous for reducing RF emissions.

Timing diagram 400 further illustrates a transition back from a low data signal to a high data signal at time $t_2$. At time $t_2$, the data signal flips back from low to high, and first wire 206-1 is connected again to a voltage source (e.g., voltage source 208). As a result, the voltage level of first wire 206-1 returns back to the first voltage level from the second voltage level.

While timing diagram 400 shows the first voltage level to be 1.2 V and the second voltage level to be 1.0 V, any suitable voltage levels may be used. Suitable voltage levels may vary depending on characteristics of a system (e.g., system 100), such as types of devices and/or a length of a connector (e.g. connector 106) connecting the two devices (e.g., first device 102 and second device 104). First device 102 may determine suitable voltage levels for each implementation of system 100. For instance, first device 102 may have a calibration phase in which first device 102 determines a suitable first voltage level and a suitable second voltage level. First device 102 may set the first and second voltage levels based on information regarding first device 102, second device 104, and/or connector 106. For example, a type of device for second device 104 may determine a voltage level needed to provide sufficient power for second device 104. Additionally or alternatively, a length of connector 106 may determine magnitudes of first and second voltage levels and/or a magnitude of a difference in first and second voltage levels needed to provide sufficient differential signaling. Such information may be input by a user and/or determined by first device 102. For instance, first device 102 may determine a length of connector 106 or suitable voltage levels by measuring voltage levels on wires of connector 106 and/or by sending messages (e.g., a command requesting a response) via various voltage levels on wires of connector 106 and checking for appropriate responses. Any other suitable techniques may be used to determine appropriate voltages for the first and second voltage level.

Additionally, in some examples, time periods during which wires are at the second voltage level may be used for back telemetry communication, so that a second device (e.g., second device 104) provides data to a first device (e.g., first device 102). As mentioned, once a pulse signal from a pulse circuit has ended, a corresponding switch (e.g., switches 218) may be opened and the wire disconnected from both a voltage source and an adjustable current source. The voltage level on the wire may be discharged to the second voltage level from the first voltage level and left floating at the second voltage level until a change in data signal. During the time period while the voltage level is left floating (e.g., a time period 410), the second device may drive the voltage level to a different, third (and/or fourth) voltage level to communicate data to the first device. For instance, the second device may drive the voltage level further down from the second voltage level to a third voltage level that is less than the second voltage level and greater than or equal to zero. A changing of the voltage level to the third voltage level may indicate a high signal from the second device to the first device, while an unchanged voltage level may indicate a low signal from the second device to the first device. The first device may detect the voltage level on the wire during the time period and thus receive data signals as transmitted by the second device. Alternatively, the second device may use the third voltage level to indicate a high signal and a fourth voltage level that is lower than the third voltage level (or higher than the second voltage level) to indicate a low signal. Any other suitable combinations of voltage levels and high/low signals may also be used in other implementations. Prior to an end of a data cycle interval from the first device, either the first device or the second device may return the voltage level of the wire back to the second voltage level. Alternatively or additionally, each data cycle interval from the first device may start with a returning the wire to the first voltage level, from which the first device may discharge the wire to the second voltage level as appropriate corresponding to the data signal to be transmitted.

An example implementation of system 100 (and/or system 200) is a cochlear implant system. In such an example, first device 102 may be implemented by a behind-the-ear unit of the cochlear implant system and second device 104 may be implemented by a headpiece of the cochlear implant system. As such, an exemplary cochlear implant system will now be described.

Figure 5:
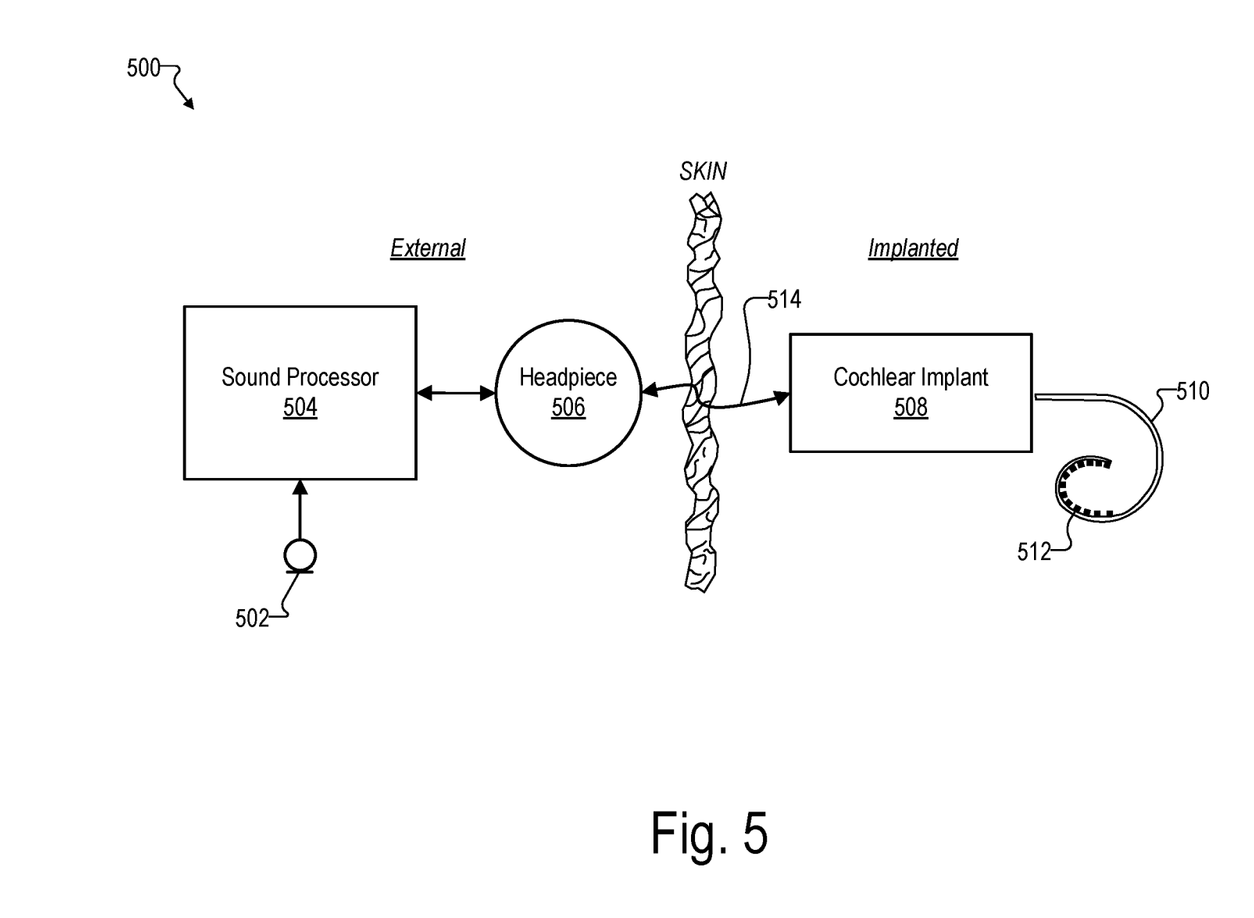
FIG. 5 illustrates an exemplary cochlear implant system according to principles described herein.

FIG. 5 illustrates an exemplary cochlear implant system 500. As shown, cochlear implant system 500 may include a microphone 502, a sound processor 504, a headpiece 506 having a coil disposed therein, a cochlear implant 508, and an electrode lead 510. Electrode lead 510 may include an array of electrodes 512 disposed on a distal portion of electrode lead 510 and that are configured to be inserted into a cochlea of a recipient to stimulate the cochlea when the distal portion of electrode lead 510 is inserted into the cochlea. One or more other electrodes (e.g., including a ground electrode, not explicitly shown) may also be disposed on other parts of electrode lead 510 (e.g., on a proximal portion of electrode lead 510) to, for example, provide a current return path for stimulation current generated by electrodes 512 and to remain external to the cochlea after electrode lead 510 is inserted into the cochlea. As shown, electrode lead 510 may be pre-curved so as to properly fit within the spiral shape of the cochlea. Additional or alternative components may be included within cochlear implant system 500 as may serve a particular implementation.

As shown, cochlear implant system 500 may include various components configured to be located external to a recipient including, but not limited to, microphone 502, sound processor 504, and headpiece 506. Cochlear implant system 500 may further include various components configured to be implanted within the recipient including, but not limited to, cochlear implant 508 and electrode lead 510.

Microphone 502 may be configured to detect audio signals presented to the user. Microphone 502 may be implemented in any suitable manner. For example, microphone 502 may include a microphone that is configured to be placed within the concha of the ear near the entrance to the ear canal, such as a T-MIC™ microphone from Advanced Bionics. Such a microphone may be held within the concha of the ear near the entrance of the ear canal during normal operation by a boom or stalk that is attached to an ear hook configured to be selectively attached to sound processor 504. Additionally or alternatively, microphone 502 may be implemented by one or more microphones disposed within headpiece 506, one or more microphones disposed within sound processor 504, one or more beam-forming microphones, and/or any other suitable microphone as may serve a particular implementation.

Sound processor 504 may be configured to direct cochlear implant 508 to generate and apply electrical stimulation (also referred to herein as "stimulation current") representative of one or more audio signals (e.g., one or more audio signals detected by microphone 502, input by way of an auxiliary audio input port, input by way of a clinician's programming interface (CPI) device, etc.) to one or more stimulation sites associated with an auditory pathway (e.g., the auditory nerve) of the recipient. Exemplary stimulation sites include, but are not limited to, one or more locations within the cochlea, the cochlear nucleus, the inferior colliculus, and/or any other nuclei in the auditory pathway. To this end, sound processor 504 may process the one or more audio signals in accordance with a selected sound processing strategy or program to generate appropriate stimulation parameters for controlling cochlear implant 508. Sound processor 504 may be housed within any suitable housing (e.g., a behind-the-ear ("BTE") unit, a body worn device, headpiece 506, and/or any other sound processing unit as may serve a particular implementation).

In some examples, sound processor 504 may wirelessly transmit stimulation parameters (e.g., in the form of data words included in a forward telemetry sequence) and/or power signals to cochlear implant 508 by way of a wireless communication link 514 between headpiece 506 and cochlear implant 508 (e.g., a wireless link between a coil disposed within headpiece 506 and a coil physically coupled to cochlear implant 508). It will be understood that communication link 514 may include a bi-directional communication link and/or one or more dedicated uni-directional communication links.

Headpiece 506 may be communicatively coupled to sound processor 504 and may include an external antenna (e.g., a coil and/or one or more wireless communication components) configured to facilitate selective wireless coupling of sound processor 504 to cochlear implant 508. Headpiece 506 may additionally or alternatively be used to selectively and wirelessly couple any other external device to cochlear implant 508. To this end, headpiece 506 may be configured to be affixed to the recipient's head and positioned such that the external antenna housed within headpiece 506 is communicatively coupled to a corresponding implantable antenna (which may also be implemented by a coil and/or one or more wireless communication components) included within or otherwise associated with cochlear implant 508. In this manner, stimulation parameters and/or power signals may be wirelessly transmitted between sound processor 504 and cochlear implant 508 via a communication link 514 (which may include a bidirectional communication link and/or one or more dedicated unidirectional communication links as may serve a particular implementation).

Cochlear implant 508 may include any suitable type of implantable stimulator. For example, cochlear implant 508 may be implemented by an implantable cochlear stimulator. Additionally or alternatively, cochlear implant 508 may include a brainstem implant and/or any other type of cochlear implant that may be implanted within a recipient and configured to apply stimulation to one or more stimulation sites located along an auditory pathway of a recipient.

In some examples, cochlear implant 508 may be configured to generate electrical stimulation representative of an audio signal processed by sound processor 504 (e.g., an audio signal detected by microphone 502) in accordance with one or more stimulation parameters transmitted thereto by sound processor 504. Cochlear implant 508 may be further configured to apply the electrical stimulation to one or more stimulation sites (e.g., one or more intracochlear regions) within the recipient via electrodes 512 disposed along electrode lead 510. In some examples, cochlear implant 508 may include a plurality of independent current sources each associated with a channel defined by one or more of electrodes 512. In this manner, different stimulation current levels may be applied to multiple stimulation sites simultaneously by way of multiple electrodes 512.

In some examples, functionality of sound processor 504 is divided into a sound processor included in headpiece 506 and another sound processor included in a BTE unit. For example, the sound processor in the BTE unit may process audio signals detected by microphone 502 to provide digital audio data. The sound processor in headpiece 506 may receive and process the digital audio data to direct cochlear implant 508 to generate and apply electrical stimulation representative of the digital audio data. Alternatively, as mentioned, sound processor 504 may be housed entirely in the BTE unit. In either case, the low-power differential communication architecture described herein may be implemented in the BTE unit to communicate with and provide power to headpiece 506.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A device comprising:
    a voltage source configured to selectively drive a first wire and a second wire with a first voltage level, the first and second wires included in a differential signaling wire pair;
    an adjustable current source configured to selectively discharge the first wire and the second wire; and
    a control circuit configured to output data and power by way of the differential signaling wire pair by:
        selectively coupling the first wire to the voltage source and the second wire to the adjustable current source such that, during a first time period, the first wire has the first voltage level and the second wire has a second voltage level less than the first voltage level and greater than zero volts; and
        selectively switching the first wire from being coupled to the voltage source to being coupled to the adjustable current source and the second wire from being coupled to the adjustable current source to being coupled to the voltage source such that, during a second time period subsequent to the first time period, the first wire has the second voltage level and the second wire has the first voltage level.

2. The device of claim 1, wherein the control circuit is further configured to set the second voltage level by controlling a characteristic of the adjustable current source.

3. The device of claim 2, wherein the characteristic includes a value of an output of the adjustable current source.

4. The device of claim 2, wherein the characteristic includes an on time of the adjustable current source.

5. The device of claim 2, wherein the control circuit is configured to determine a value of the characteristic by:
    measuring the second voltage level;
    comparing the second voltage level to a predetermined voltage level; and
    adjusting, based on the comparing, the value of the characteristic.

6. The device of claim 2, wherein the control circuit is configured to determine a value of the characteristic by:
    selecting a first value of the second voltage level;
    sending a command by way of the differential signaling wire pair using the first value of the second voltage level; and
    selecting, based on whether a response to the command is received, a second value of the second voltage level.

7. The device of claim 1, wherein the control circuit is further configured to set the second voltage level by controlling an amount of time the second wire is selectively coupled to the adjustable current source.

8. The device of claim 7, wherein the control circuit further comprises a pulse circuit configured to control the amount of time.

9. The device of claim 8, wherein the pulse circuit comprises a delay locked loop (DLL).

10. The device of claim 7, wherein the amount of time is a portion of a length of the first time period.

11. The device of claim 10, wherein during a remainder of time of the length of the first time period, the second wire is uncoupled from the adjustable current source.

12. The device of claim 11, wherein, during the remainder of time, the second voltage level is maintained by a capacitance on the second wire.

13. The device of claim 11, wherein, during the remainder of time, the second wire is configured to be set to a third voltage level different from the first voltage level and the second voltage level by another device.

14. The device of 1, wherein the first device is a behind-the-ear (BTE) unit of a cochlear implant system and the second device is a headpiece of the cochlear implant system.

15. A system comprising:
    a first device; and
    a second device coupled to the first device by a differential signaling wire pair comprising a first wire and a second wire,
    the first device comprising:
        a voltage source configured to selectively drive the first wire and the second wire with a first voltage level;
        an adjustable current source configured to selectively discharge the first wire and the second wire; and a control circuit configured to output data and power by way of the differential signaling wire pair by:
  selectively coupling the first wire to the voltage source and the second wire to the adjustable current source such that, during a first time period, the first wire has the first voltage level and the second wire has a second voltage level less than the first voltage level and greater than zero volts; and
  selectively switching the first wire from being coupled to the voltage source to being coupled to the adjustable current source and the second wire from being coupled to the adjustable current source to being coupled to the voltage source such that, during a second time period subsequent to the first time period, the first wire has the second voltage level and the second wire has the first voltage level;

the second device comprising:
  a receiving circuit configured to:
    receive the data and the power by way of the differential signaling wire pair; and
    transmit the data by way of a radio frequency (RF) transmitter.

16. The system of claim 15, wherein:
the control circuit is further configured to set the second voltage level by controlling an amount of time the second wire is selectively coupled to the adjustable current source, the amount of time being a portion of a length of the first time period;
the second device further comprises a transmitting circuit configured to output additional data to the first device by way of the differential signaling wire pair by:
  selectively driving the second wire to a third voltage level that is different from the first voltage level and the second voltage level during a remainder of time of the length of the first time period.

17. The system of claim 15, wherein the first device is a behind-the-ear (BTE) unit of a hearing system and the second device is a headpiece of the hearing system.

18. A cochlear implant system comprising:
an implant configured to apply electrical stimulation representative of one or more audio signals to an auditory pathway of a user;
a headpiece including a transmitter configured to wirelessly transmit power and data to the implant;
an external unit coupled to the headpiece by a differential signaling wire pair comprising a first wire and a second wire, the external unit comprising:
  a voltage source configured to selectively drive the first wire and the second wire with a first voltage level;
  an adjustable current source configured to selectively discharge the first wire and the second wire; and
  a control circuit configured to output data and power by way of the differential signaling wire pair by:
    selectively coupling the first wire to the voltage source and the second wire to the adjustable current source such that, during a first time period, the first wire has the first voltage level and the second wire has a second voltage level less than the first voltage level and greater than zero volts; and
    selectively switching the first wire from being coupled to the voltage source to being coupled to the adjustable current source and the second wire from being coupled to the adjustable current source to being coupled to the voltage source such that, during a second time period subsequent to the first time period, the first wire has the second voltage level and the second wire has the first voltage level.

19. The system of claim 18, wherein:
the control circuit is further configured to set the second voltage level by controlling an amount of time the second wire is selectively coupled to the adjustable current source, the amount of time being a portion of a length of the first time period;
the headpiece further comprises a transmitting circuit configured to output additional data to the BTE by way of the differential signaling wire pair by:
  selectively driving the second wire to a third voltage level that is different from the first voltage level and the second voltage level during a remainder of time of the length of the first time period.

20. The system of claim 19, wherein the control circuit further comprises a pulse circuit including a delay locked loop (DLL) configured to control the amount of time.

\* \* \* \* \*